United States Patent [19]

Henriksen

[11] 4,168,431
[45] Sep. 18, 1979

[54] MULTIPLE-LEVEL X-RAY ANALYSIS FOR DETERMINING FAT PERCENTAGE

[75] Inventor: Inge B. Henriksen, Stavanger, Norway

[73] Assignee: The Kartridg Pak Co., Davenport, Iowa

[21] Appl. No.: 867,364

[22] Filed: Jan. 6, 1978

[51] Int. Cl.² ............................................. G01N 23/00
[52] U.S. Cl. ................................. 250/358 R; 250/252
[58] Field of Search ........... 250/358 R, 358 T, 358 P, 250/359, 360, 252, 272

[56] References Cited

U.S. PATENT DOCUMENTS

| | | | |
|---|---|---|---|
| 2,983,819 | 6/1958 | Bigelow et al. | 250/358 R |
| 2,992,332 | 7/1961 | Madigan | 250/358 R |
| 3,417,244 | 12/1968 | Kramer | 250/358 R |

Primary Examiner—Craig E. Church
Assistant Examiner—Thomas P. O'Hare
Attorney, Agent, or Firm—Lockwood, Dewey, Alex & Cummings

[57] ABSTRACT

A method and apparatus is provided for determining in a non-destructive manner the quantities of components in a material having irregular surfaces and which may be of a non-uniform size and of a variable consistency. Three or more beams of polychromatic X-rays, each at a different level of energy, are passed through the material, and the measurements of each incident beam and each transmitted beam are utilized in determining the percentage of one or more of the components after having substantially eliminated so-called beam-hardening effects which otherwise limit the utility of polychromatic beams.

18 Claims, 3 Drawing Figures

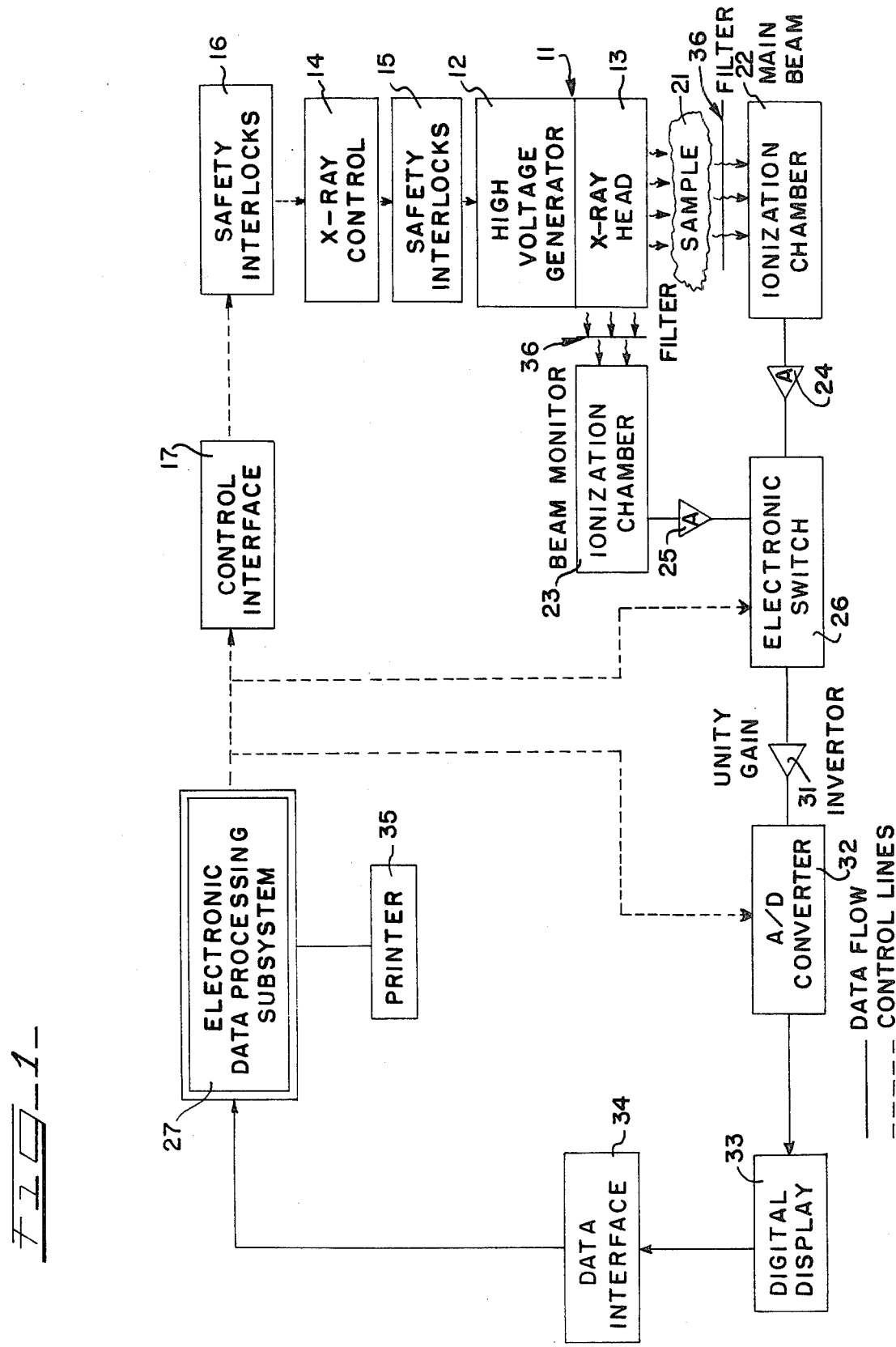

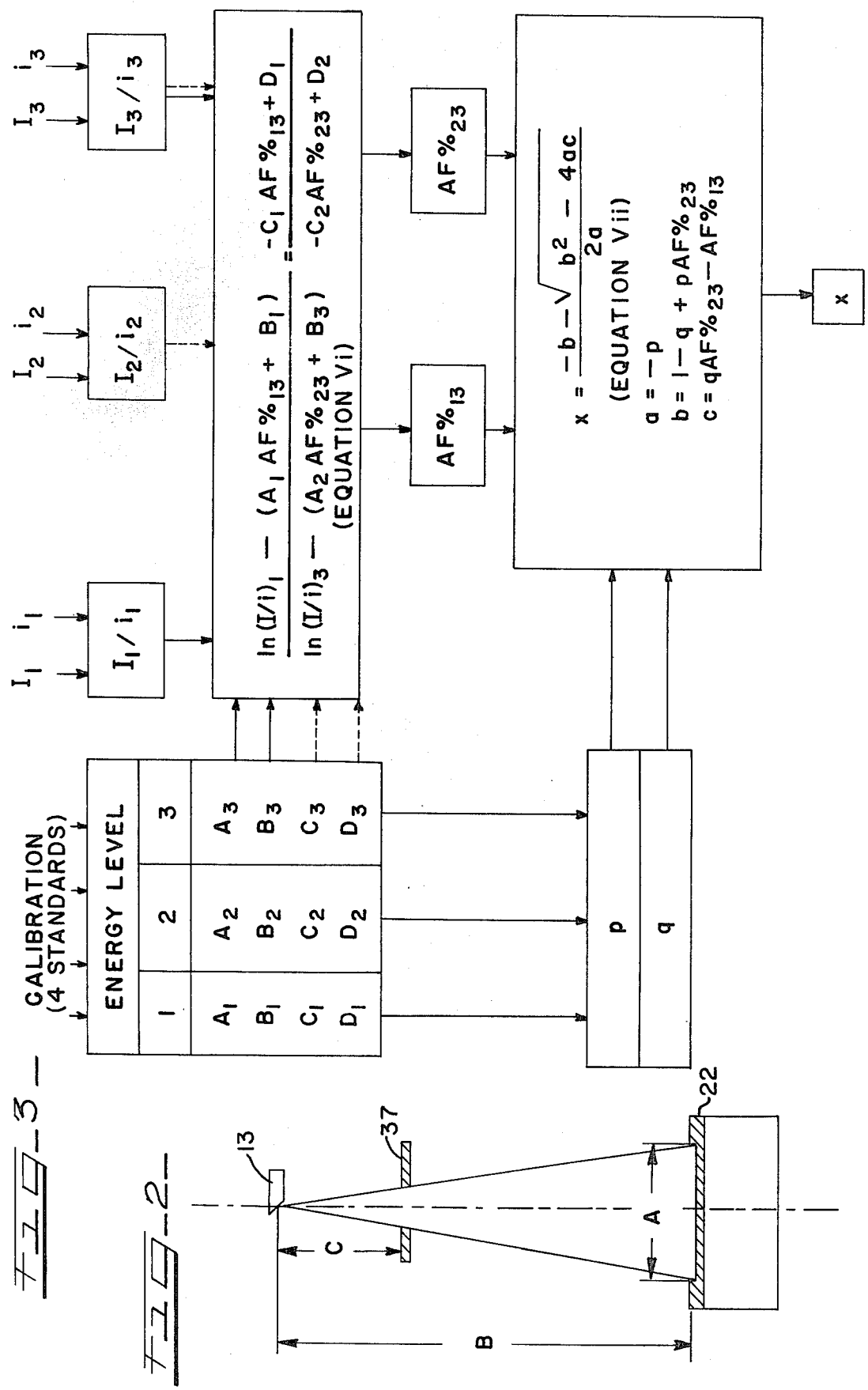

MULTIPLE-LEVEL X-RAY ANALYSIS FOR DETERMINING FAT PERCENTAGE

BACKGROUND AND DESCRIPTION OF THE INVENTION

The present invention relates generally to innovations and improvements in the quantitative analysis of components within a material and is especially suited to the analysis of the fat content of meats.

Using X-ray beams to determine relative amounts of components within materials, such as the quantity of fat within meat, are known, for example, from Madigan U.S. Pat. No. 2,992,332, which deals with determining the quantitative relationship between meat components by measuring gamma ray penetration thereof. Systems of this type use a single, polychromatic radiation beam, and they are limited in their usefulness by the need to first obtain a sample of the material being analyzed which is of a uniform predetermined weight and then to mold that sample to a predetermined uniform size having a precise geometrical configuration. Developments such as these recognize that one of the components in a particular system has an effective atomic number greater than that of another component; for example, in meat, lean meat has a high concentration of moisture and protein and includes nitrogen and oxygen atoms which are of a greater atomic number than the carbon and hydrogen atoms which predominate in the fat component, meaning that the lean meat component absorbs gamma radiation to a far greater extent than does the fat component when the gamma rays are within that range where the X-ray energy incident upon the meat is attenuated as a result of a phenomenon known as the photoelectric effect.

Copending U.S. Ser. No. 843,702, filed Oct. 19, 1977 by William H. Groves and Andrew E. Donovan for Two-Level X-Ray Analysis for Determining Fat Percentage, herein incorporated by reference, recognizes the previously known general principle that beam attenuation measurements may be conducted at two different energy levels, rather than at a single level when using monochromatic beams. Monochromatic beams are usually generated by radioactive nuclides or radionuclides, which are released as an electron moves from one atomic "shell" to another. Monochromatic beams are very easy to characterize especially when compared with polychromatic beams, such as the X-rays generated by Coolidge tubes.

Polychromatic beams result in a continuous energy spectrum characterized by the excitation potential applied to the tube, sometimes producing secondary radiation which may have a different energy spectrum and a different direction of propagation relative to the primary beam. As a polychromatic beam passes through a sample, its intensity is attenuated with the lower energy fraction of the beam being attenuated to the highest degree, causing a continuous change in the average energy level of the beam as it passes through increasing sample thicknesses, which is a well-recognized effect referred to as "beam hardening" and is considered to be one of the major disadvantages in attempting to use polychromatic beams in X-ray absorptiometry. Said copending application of Groves and Donovan describes the use of polychromatic beams at two different energy levels in a manner which significantly reduces inaccuracies resulting from the "beam hardening" effect.

There exists a significant need for avoiding the inflexibility of systems such as Madigan which are most advantageously used in the random sampling of products capable of being molded, one of the most common uses being in evaluating the fat content of ground meat formulations. This need is not completely fulfilled by Groves and Donovan, which affords significantly increased flexibility over Madigan because Groves and Donovan can analyze heterogenous materials having non-uniform weights and sizes so long as they have relatively smooth surfaces.

The present invention overcomes the disadvantages of inflexibility in the single energy level devices while at the same time eliminating the need of Groves and Donovan to smooth the material being analyzed if it does not have relatively smooth surfaces, meaning that the present invention provides a rapid, accurate and non-destructive means and method of analysis that requires no sample preparation, calls for only a minimum of sample handling, and can be used on meat that is fresh or frozen and that has been boxed or bagged at the meat packing plant level.

It is accordingly a general object of the present invention to provide an improved means for determining the relative quantities of the components of a heterogeneous material.

Another object of the present invention is an improved method and apparatus using polychromatic beams at three or more different energy levels in order to analyze the content of the components in a primarily two-component material.

Another object of this invention is an improved method and apparatus utilizing three different energy levels for determining the fat content of meat products having variable physical properties, primarily as embodied by the density and thickness of the various samples, as well as having surface roughness.

Another object of this invention is an improved method and apparatus utilizing four different energy levels for the fat content of meat products having variable physical properties, as well as having surface roughness and variable fat distribution.

Another object of the present invention is an improved method and apparatus which can be operated by relatively unskilled labor and under plant operation conditions by scanning meats that are sold as commodity items.

Another object of the present invention is an improved method and apparatus which includes calibration standards at three or more energy levels for accurately and automatically determining the fat content of primarily two-component materials such as meat.

These and other objects of the present invention will be apparent from the following detailed description, taken in conjunction with the accompanying drawing wherein:

FIG. 1 is a schematic illustration of the preferred apparatus of the present invention;

FIG. 2 is an enlarged schematic detail view of the filtering means shown in FIG. 1; and FIG. 3 is a flow diagram of computations undergone in the operation of the apparatus of FIG. 1.

This invention recognizes that, in general, there are three or more variables that can influence the degree of attenuation of radiation transmission readings: absorption coefficient of the particular sample (which is related to the percent fat in a meat sample), the density and thickness of the sample being penetrated, and the surface roughness of the sample. Another variable is the distribution of the components within the sample. It also recognizes that the density, thickness, surface roughness, and component distribution variables for any one sample will not be changed at different radiation energy levels and that the absorption coefficient will change at each radiation energy level. I have discovered and verified that detected changes in transmitted signal between three or more signals at different radiation energy levels are due to the difference in the absorption coefficients which are related to the component percentages of the sample; this assumes there are predictable responses from the detector used at three or more different radiation energy levels. Such an assumption is supported by the present invention which substantially eliminates inaccuracies expected from polychromatic sources, in which the responses will vary, by comparing the observed responses of radiation for an unknown sample at a particular energy level with calibration standards responses that have been determined for a known sample at that same energy level, whereby these combined readings at three different respective energy levels will dictate a single condition of surface roughness, density, thickness, and percentage composition.

When a fourth energy level is added, a single condition of component distribution can also be realized. To avoid confusion in this specification, all references to three energy levels will be understood to apply generally to three or more energy levels, and all references to surface roughness or irregularity conditions will be understood to apply generally to additional variable conditions, such as component distribution, in a multi-component system.

It is believed that this comparative response approach is valid because a comparison between the known composition and other parameters of the calibration standards and the unknown composition and corresponding other parameters of the sample being analyzed at three different radiation levels will show, on a relative basis, a set of readings which relate to the unknown composition percentages. Since the composition percentages are the same when read at the three different energy levels, the readings are equal to the effect of the changes in transmitted radiation observed for each possible composition percentage mixture. The unknown composition percentages can be calculated by comparing them with the changes in transmitted radiation observed for the known calibration sample.

It is to be noted that X-ray radiation energy is specified in terms of eVp (peak electron volts) or KeVp (peak Kilo electron volts) referring to the excitation potential that is applied to the polychromatic beam generating tube; the effective energy of the continuous spectrum generated by the tube, or its "effective wavelength" (KeVeff), is significantly lower than the excitation potential applied to the tube. For example, an excitation potential of 20 KeVp corresponds to 13 KeVeff, 30 KeVp corresponds to 20 KeVeff, 40 KeVp to 27 KeVeff, 60 KeVp to 40 KeVeff, 90 KeVp to 60 KeVeff, and 100 KeVp to 67 KeVeff.

The preferred apparatus shown in FIG. 1 includes polychromatic radiation generating means of a known type, indicated generally by 11, which includes a high voltage generator 12 and an X-ray tube or head 13, the generator 12 being variably activated by an X-ray control means 14 operatively interconnected through safety interlocks 15, 16. Control interface 17 provides for initiation and serialization of the process. Appropriate means of known design are also provided for entering data required during calibration process.

The radiation generating means 11 is capable of serial variation between three different polychromatic energy levels, the polychromatic beams being passed from head 13 to a sample 21 that is being analyzed. Ionization chamber 22 monitors the attenuated polychromatic rays passing through item 21. A beam monitor ionization chamber 23 is also in association with the radiation generating means 11, preferably at a 90° angle as shown, to act in simultaneous cooperation with ionization chamber 22, and thereby detect any changes in beam intensity that might be caused by fluctuations in the line voltage and in the filament current, and by heat accumulation in the apparatus, and the like. Details concerning X-ray tubes and electronic circuitry are disclosed in said Madigan U.S. Pat. No. 2,992,332, which is herein incorporated by reference.

Intensity readings pass from chambers 22 and 23 through linear amplifiers 24 and 25, respectively. These linear amplifiers can be operated over several decades of input signal levels as may be produced by the ionization chambers 22 and 23.

Then the intensity readings pass into an electronic switch 26 for ultimate passage to an electronic data processing subsystem 27. The preferred data processing subsystem 27 includes a Hewlet-Packard 9815-A programable calculator; other suitable computer means may be substituted therefor, such as a Motorola 6800 series system or an IBM 370 model computer. Electronic data processing subsystem 27 is programmed to perform the calibration and the percent fat computation functions for each unknown sample 21. Conventional interconnections between the subsystem 27 and the electronic switch 26 are provided, including a unity gain invertor 31, an A/D converter 32, a digital display 33, and a data interface 34. Various data generated through the subsystem 27 are reported at printer 35.

Generally, in order to maintain consistency and in order to avoid variations from one piece of equipment to another, it is preferred that this apparatus be arranged as described and shown in FIG. 1 whereby the same piece of apparatus generates the X-ray beams at each of the energy levels in a serial fashion. This will minimize the chance that unanticipated changes in a piece of equipment involved in generating one of the energy levels will be interpreted by the apparatus as being attributed to the amount of one of the components in the sample 21.

When the higher energy levels are being used, such as intensity readings at or above 60 KeVp, it is preferable to include filtering means 36 in both the monitor beam and the sample beam from X-ray head 13. Filtering means 36 purposely hardens the high energy level beams to eliminate soft or low energy from passing to the ionization chambers 22 and 23, which soft energy would result in data that interferes with the lower levels of energy transmission.

As shown in FIG. 2, a lead ring 37 collimates the X-ray beam so the beam diameter at the detector level is substantially equal to the opening A in the detector or ionization chamber 22, 23. For example, an X-ray source positioned 40 cm from head 13 (distance B) will be masked by an ⅛-inch thick ring 37 having a collimating opening diameter of 3.75 cm positioned approximately 10 cm from head 13 (distance C) down from its normal diameter of about 20.3 cm to 15 cm (distance A). This masking is done to eliminate an apparent energy level dependency at the detector edge; it utilizes narrow beam geometry to reduce the effects of scattering.

In accordance with the method of the present invention, the quantitative relationship of components in a primarily 2-component material is determined without destroying the material or sample, the components varying from each other in atomic structure. Such a material may be, for example, in the form of unmodified commercial ground meat or "boxed" meat, either frozen or fresh, having an irregular surface configuration, weight and shape, making practical the in situ analysis thereof at any stage of its processing. A beam of polychromatic X-ray radiation at one energy level is then passed through the material, while monitoring both the incident beam and the attenuated beam that has passed through the material. This same operation is performed also with a second and then a third polychromatic X-ray beam, each having an incident energy level different from that of the first beam and from each other. After accounting for beam hardening of the polychromatic beams, the quantitative relationship between the two components of the material are determined by solving three simultaneous independent equations for the percentage content of one of said components.

Since X-ray absorption for a material being analyzed, as defined by the absorption coefficient, varies exponentially with the energy of the source, interrelated relationships between the surface configuration of the sample and the relative amounts of the components thereof are produced at each energy level, as are relationships between the thickness of the sample material and the relative amounts of the components, making it possible to use three different mathematical functions to eliminate both the surface configuration variable and the thickness variable, solving the functions simultaneously for the amount of one of the components. The method of this invention eliminates the need for smoothing the surface of the sample, as well as the need for precise sample weight and container shape and size, to thereby remove these restrictions as a source of random error and/or fixed bias in the system.

It is not possible to obtain accurate analyses by simply using a polychromatic X-ray source at three different energy levels, recording the main beam and monitor beam data, and inserting this data into three simple functions. This is due in part to the beam hardening phenomenon characteristic of polychromatic X-rays as they undergo a continuous change in average energy level while the beam is attenuated by the material.

It has been observed that a direct reading of the incident beam will result in an incident beam reading that is too high because too large a portion of the lower energy fraction of the polychromatic beam will be detected, although it will not have any significant penetration through the material, and thus will be essentially completely attenuated by most materials. This change in value of the incident beam is a function of the sample's composition. This relationship can be expressed as:

$$\ln(I_0) = Ax + B \qquad \text{(Equation i)}$$

where $I_0$ is the detected intensity of the incident beam, where x is the percentage of one of the components, such as the fat component of meat; and where A and B are calibration constants.

When Equation i is modified to take into account changes in an X-ray beam on passing through the sample being analyzed, the equation, in its simplest form, may be expressed as follows:

$$\ln(I/I_0) = -[(-Cx+D)T - \tfrac{1}{2}\sigma^2(-Cx+D)] \qquad \text{(Equation ii)}$$

where $I_0$ and x are as defined hereinbefore, I is the intensity of the beam after transmission through the product, C and D are different calibration constants, T is the average thickness of the product being analyzed, and $\sigma^2$ is the variance of the thickness distribution. It will be noted that when the sample surface is smooth, $\sigma^2$ will equal zero. A simultaneous solution to remove the average thickness variable and the thickness distribution variable is made possible by developing two other substantially identical functions each having its own calibration constants for $I_0$ and I of two other different polychromatic X-ray beams.

The disadvantage of beam hardening can be controlled in accordance with the preferred method which involves the use of a plurality of calibration standards at each of the three energy levels being utilized in the method for empirically determining appropriate calibration constants. Preferred calibration standards are sandwiches of two materials having different molecular densities such as plexiglass and aluminum which can be directly correlated to the products being analyzed, such as the fat content of meat. It is also possible to use calibration standards made of the precise type of product to be analyzed, such as meat samples of known fat contents. The use of meat as a calibration standard, however, has the disadvantages of being a material that can deteriorate over time and that is not easily and conveniently handled, especially in a plant-scale operation.

A methyl acrylic polymer, such as Plexiglas (Rohm and Haas Company) falls within a preferred class of polymer materials having a carbon-oxygen ratio which can simulate the X-ray absorption characteristics of meats and that have X-ray absorption characteristics that are relatively consistent with meat over the range of energy levels found to be especially useful in the analysis operation of this invention. Aluminum is believed to be useful because of its atomic structure. It can be used in conjunction with a polymer material such as Plexiglas to provide a high degree of flexibility in designing calibration standards having a wide range of absorption characteristics.

A grouping of calibration standards, called a standards matrix, consists of a plurality of sandwiches each of a known equivalent percent fat value, thickness and density. It is believed to be advantageous to select calibration standards having composition equivalents and thickness in a range generally close to that of the actual products such as meat samples to be analyzed, to assist in the reduction of beam hardening effects brought about as the polychromatic X-ray beams pass through the samples and change in effective intensity.

A more rigorous expression of the simultaneous equations represented by Equation ii includes four calibration constants at each energy level; this requires four calibration standards in the standards matrix in order to establish the value for each of the total of twelve calibration constants needed. This more rigorous expression of the three simultaneous equations is as follows:

$$\ln(I_1) - (A_1 x + B_1) = -C_1 x + D_1[-T - \tfrac{1}{2}\sigma^2(-C_1 x + D_1)] \qquad \text{(Equation iii)}$$

$$\ln(I_2) - (A_2 x + B_2) = -C_2 x + D_2[-T - \tfrac{1}{2}\sigma^2(-C_2 x + D_2)] \quad \text{(Equation iv)}$$

$$\ln(I_3) - (A_3 x + B_3) = -C_3 x + D_3[-T - \tfrac{1}{2}\sigma^2) - C_3 x + D_3)] \quad \text{(Equation v)}$$

where, by Equation i, $A_1 x + B_1 = \ln(I_0)_1$, $A_2 x + B_2 = \ln(I_0)_2$ and $A_3 x + B_3 = \ln(I_0)_3$; where A, B, C and D are constants and x, T, $\sigma^2$, I and $I_0$ are as hereinbefore defined; and where subscripts 1, 2 and 3 refer to energy levels 1, 2 and 3, respectively. Two values for x are obtained by combining and solving any two pairs of Equations iii, iv and v. These two values for x are then used in computing the fat content of the sample in accordance with this invention.

FIG. 3 illustrates the computations involved in obtaining the value of x, or the fat percent value, which are preferably carried out with the electronic data processing subsystem 27. Subscripts 1, 2 and 3 refer to the three energy levels; "I" and "i" refer to sample beam and beam monitor readings, respectively. $AF\%_{13}$ refers to the intermediate or apparent fat percent developed between energy levels 1 and 3. $AF\%_{23}$ refers to the intermediate or apparent fat percent developed between energy levels 2 and 3. These intermediate or apparent fat percentages are obtained by treating samples with irregular surfaces as if they were obtained with a smooth sample. Other energy pairings, such as 1 and 2, can be substituted for those illustrated.

The preferred computation sequence begins by emitting energy level 1 at 28 KeVp, collecting sample beam and beam monitor readings, $I_1$ and $i_1$. Next, energy level 2 at 40 KeVp is emitted and readings $I_2$ and $i_2$ are made. Filter means 36 are inserted prior to emitting energy level 3 at 60 KeVp and readings $I_3$ and $i_3$ are arrived at. Four calibration standards of known X-ray absorption characteristics are used to solve an equation incorporating the relationships of Equations iii, iv and v in order to determine the respective calibration constants at each of the three energy levels.

Such respective calibration constants serve as a basis for calculating "p" and "q", which are the slope and intercept, respectively, of the equation relating the calibration constants. Meanwhile, the apparent fat percentage $AF\%_{13}$ is calculated from the calibration constants $A_1 \ldots D_1$ and $A_3 \ldots D$ and from the $I_1/i_1$ and $I_3/i_3$ values by means of Equation vi specified in FIG. 3. Then, the fat percentage value (x) for the particular sample being analyzed is found through Equation vii shown in FIG. 3.

The choice of optimum energy sets is complex; however, some basic constraints must be adhered to. The highest energy level can be as strong as 120 KeVp. A practical upper limit and the preferred highest energy level is 60 KeVp, since voltages above this level require significantly more radiation shielding and electrical insulation than at or below this level without yielding significant improvements in the system. The lowest energy level can be as weak as 20 KeVp, determined primarily by the sensitivity of available detection equipment and by the ability of the energy to pass through the sample. A practical lower limit has been found to be 26 KeVp because of the need to limit X-ray tube beam current to an acceptable value and the sensitivities of the detectors used. Within this range, it has been found that widely separated values, approximating the extremes provided the best resolution. The preferred three energy levels are at 28, 40 and 60 KeVp.

The following specific examples will more precisely illustrate the invention and teach the procedures presently preferred for practicing the same. While these examples relate to fat determination in meat, this invention may be used in other applications, for example in determining the fat content of fish and milk or of other fresh or processed foods, in determining the solvent or solute content of solutions, and in determining the oil content of seed plants, so long as the item being analyzed has components of different atomic structures.

EXAMPLE 1

An apparatus in accordance with FIG. 1 included a Hewlett-Packard 9815-A calculator programmed to automatically conduct the calibration and sample measurements, next calculate all of the calibration constants, and then make the final computation for x (percent fat in a meat sample). The first energy level was 28 KeVp, the second was 40 KeVp, and the third was 60 KeVp. Two meat samples V and W of known but differing compositions having random surface structure and thickness were analyzed by the apparatus and by soxhlet extraction (AOAC method 24.005[a]—1975) in order to develop calibration constants for these samples (Equations iii, iv and v) as follows: at 28 KeVp: $A_1 = 3.4234 \times 10^{-3}$, $B_1 = 6.2919$, $C_1 = 1.3978 \times 10^{-3}$ and $D_1 = 0.4565$; at 40 KeVp: $A_2 = 2.4770 \times 10^{-3}$, $B_2 = 2.593$, $C_2 = 0.7908 \times 10^{-3}$ and $D_2 = 0.3295$; and at 60 KeVp: $A_3 = 0.1407 \times 10^{-3}$, $B_3 = 1.471$, $C_3 = 0.1897 \times 10^{-3}$ and $D_3 = 0.2008$, which lead to a determination that $p = -1.22 \times 10^{-3}$ and $q = 1.389$. These calibration constants were keyed to plexiglass-aluminum sandwiches that were thus available as calibration standards.

The same meat samples used in developing the calibration constants for the calibration standards were then analyzed by the apparatus in numerous additional runs, each time after making irregular surfaces by either randomly dumping portions of each sample or by intentionally manipulating the meat sample so its surface would have various thickness distributions. In either case the sample irregularity was influenced by internal voids and variable packing or density. The apparatus performed quite well as would be expected since in this particular example the calibration standards were set by the soxhlet data of the samples themselves. Table I lists the numerous irregular configuration runs for each of sample V (Run Nos. 1–11) and sample W (Run Nos. 12–18), showing the intermediate or apparent fat percentages between energy levels 1 and 3 ($AF\%_{13}$) and between energy levels 2 and 3 ($AF\%_{23}$) as well as the fat percentage (x) calculated from p, q, $AF\%_{13}$ and $AF\%_{23}$ using the relationships shown in FIG. 3. Table I average fat percent values for sample V were $16.1 \pm 0.64$, while the soxhlet percent fat was $16.4 \pm 0.40$. Average percent fat values for sample W were $30.1 \pm 0.59$, while the soxhlet percent fat was $30.3 \pm 0.55$. Neither difference is statistically significant, and the "within method" standard deviations compare favorably with standard deviations judged acceptable for soxhlet extraction techniques.

Table I

|  | Run No. | $AF\%_{13}$ | $AF\%_{23}$ | x(%) |
| --- | --- | --- | --- | --- |
|  | 1 | 19.9 | 18.7 | 15.5 |
|  | 2 | 20.3 | 19.3 | 16.6 |
|  | 2 | 20.0 | 19.1 | 16.7 |
| Sample | 4 | 22.2 | 20.4 | 16.8 |

Table I-continued

|  | Run No. | AF%₁₃ | AF%₂₃ | x(%) |
|---|---|---|---|---|
| "V" | 5 | 23.5 | 21.4 | 15.7 |
|  | 6 | 22.0 | 20.6 | 16.8 |
|  | 7 | 23.5 | 21.2 | 15.0 |
|  | 8 | 23.3 | 21.4 | 16.3 |
|  | 9 | 28.1 | 25.0 | 16.6 |
|  | 10 | 26.7 | 23.7 | 15.6 |
|  | 11 | 24.5 | 22.1 | 15.6 |
| Sample "W" | 12 | 35.4 | 34.0 | 30.0 |
|  | 13 | 35.2 | 33.8 | 29.8 |
|  | 14 | 39.1 | 36.8 | 30.3 |
|  | 15 | 44.4 | 40.4 | 29.1 |
|  | 16 | 37.1 | 35.3 | 30.2 |
|  | 17 | 35.7 | 34.4 | 30.7 |
|  | 18 | 35.1 | 34.0 | 30.9 |

EXAMPLE 2

The apparatus used in and the calibration standards developed in Example 1 were subjected to testing with three additional meat samples X, Y and Z as well as with sample W from Example 1. Sample W (Run Numbers 22-28) was meat having about 30% fat that was passed through a grinding plate having a ⅛ inch hole size. Sample X (Run Nos. 17-21) was meat of about 10% fat passed through a ⅛ inch grinding plate. Sample Y (Run Nos. 11-16) was meat of about 6% fat passed through a ⅛ inch grinding plate. Sample Z (Run Nos. 1-10) was meat cut into cubes approximately 1 inch on an edge and of about 7% fat. Numerous runs of each sample were made, some runs made with the irregular surface structure of the unmodified sample and others made after smoothing the surface structure by trowelling it to substantially eliminate air pockets, mounds or declivities in excess of ¼ inch in size. X-ray measurements conducted on these samples were used to calculate AF%₁₃ and AF%₂₃ values, from which the percent (x) values are determined according to the relationships of FIG. 3. Table II tabulates these values.

Calibration constants for this Example which were developed from the calibration standards were as follows: at 28 KeVp: $A = 4.2725 \times 10^{-3}$, $B = 6.2709$, $C = 1.3560 \times 10^{-3}$ and $D = 0.4554$; at 40 KeVp; $A = 2.6760 \times 10^{-3}$, $B = 2.5948$, $C = 7.9305 \times 10^{-4}$ and $D = 0.3300$; and at 60 KeVp; $A = 4.1025 \times 10^{-4}$, $B = 1.4693$, $C = 1.7281 \times 10^{-4}$ and $D = 0.2006$. The average Table II fat percent value for sample Z was 6.8%±0.86, while the soxhlet value was 6.6%. For sample Y the average was 6.4%±0.58, the soxhlet value being 6.4%. For sample X the average was 9.7%±0.40, while the soxhlet value was 9.5%. For sample W the average was 30.7%±0.28, and its soxhlet value was 30.3%.

The overall standard deviation for all of Run Nos. 1-28 was ±0.61, in this instance being equal to the standard deviation (±0.61) obtained with the soxhlet extraction correlations run on these samples, and which compares quite favorably with reported soxhlet extraction standard deviations. Pettinati, et al., "Rapid Determination of Fat in Meat and Meat Products by Foss-let Solvent Extraction and Density Measurements", *J. AOAC* 58 (6), 1975 reports a soxhlet standard deviation of ±0.54%; and the American Meat Institute reports that standard deviations ranged from ±0.75% to ±0.87% for various collaborative studies involving more than 100 laboratories over the years 1970 to 1973, "Precision Probable in Analysis for Fat, Moisture and Protein in Meat Labs", *Anyl Ray Corp. Bulletin No. 508* (1975). All of this indicates that there is no bias in the calibration and that the present invention has very good reproducibility as a system for rapid, non-destructive analysis requiring no sample preparation and minimal sample handling.

Table II

|  | Run No. | Surface Structure | AF%₁₃ | AF%₂₃ | X (%) |
|---|---|---|---|---|---|
| Sample "Z" | 1 | smooth | 9.7 | 9.0 | 7.1 |
|  | 2 | " | 10.2 | 9.5 | 7.6 |
|  | 3 | " | 9.9 | 8.7 | 5.5 |
|  | 4 | " | 10.3 | 9.1 | 5.9 |
|  | 5 | irreg. | 10.9 | 9.6 | 6.1 |
|  | 6 | " | 15.9 | 13.4 | 6.8 |
|  | 7 | " | 18.5 | 15.2 | 6.4 |
|  | 8 | " | 15.8 | 13.5 | 7.4 |
|  | 9 | " | 18.3 | 15.5 | 8.0 |
|  | 10 | " | 11.8 | 10.7 | 7.9 |
| Sample "Y" | 11 | smooth | 8.8 | 8.3 | 7.0 |
|  | 12 | " | 8.9 | 8.6 | 5.4 |
|  | 13 | " | 9.3 | 8.4 | 6.0 |
|  | 14 | irreg. | 12.4 | 10.8 | 6.5 |
|  | 15 | " | 11.7 | 10.3 | 6.6 |
|  | 16 | " | 13.7 | 11.8 | 6.7 |
| Sample "X" | 17 | smooth | 13.6 | 12.4 | 9.2 |
|  | 18 | " | 13.8 | 12.7 | 9.8 |
|  | 19 | irreg. | 14.0 | 13.0 | 10.3 |
|  | 20 | " | 17.8 | 15.6 | 9.7 |
|  | 21 | " | 16.1 | 14.3 | 9.5 |
| Sample "W" | 22 | smooth | 36.1 | 34.7 | 30.8 |
|  | 23 | irreg. | 39.8 | 37.3 | 30.4 |
|  | 24 | " | 37.1 | 35.4 | 30.7 |
|  | 25 | " | 37.6 | 35.7 | 30.4 |
|  | 26 | " | 38.6 | 36.6 | 31.1 |
|  | 27 | " | 41.9 | 39.0 | 31.0 |
|  | 28 | " | 39.2 | 36.9 | 30.5 |

It will be apparent to those skilled in this art that this present invention can be embodied in various forms; accordingly, this invention is to be construed and limited only by the scope of the appended claims.

I claim:

1. An apparatus for determining the quantitative relationship of components in an item composed primarily of two components varying from each other in molecular makeup, the apparatus being capable of analyzing items variable in surface roughness, weight, density, thickness, and overall geometrical configuration comprising:

means for generating a first incident beam of polychromatic X-ray radiation at a first preselected tube excitation potential and for directing it toward an item composed primarily of two components, means for generating a second incident beam of polychromatic X-ray radiation at a second preselected tube excitation potential and for directing it toward said item;

means for generating a third incident beam of polychromatic X-ray radiation at a third preselected tube excitation potential and for directing it toward said item to combine with the first and second beams to provide inputs useful in substantially eliminating, while determining the quantitative relationship of the components, effects of inaccuracies that are introduced by surface roughness of items;

means for monitoring, detecting and measuring intensity values of each of the beams after they pass through said item;

means for determining calibration values at each of said preselected tube excitation potentials; and a means for processing said intensity values measured for the item together with the calibration values for automatically and accurately calculating the percentage of one of said components of the item irrespective of surface roughness of the item and the polychromatic nature of said three generating means.

2. The apparatus of claim 1, wherein said polychromatic radiation generating means includes a high voltage generator, an X-ray tube, and a control means for variably activating the generator between at least said three preselected tube excitation potentials.

3. The apparatus of claim 1, further comprising a beam monitor ionization means in association with the means for generating incident beams of polychromatic radiation, said beam monitor ionization means being for simultaneous cooperation with said incident beams generating means to detect fluctuations in intensity of the incident beams.

4. The apparatus of claim 1, further comprising an electronic data processing subsystem including said means for determining calibration values and said means for processing the intensity values and calibration values.

5. The apparatus of claim 1, further comprising a filtering means between said means for generating polychromatic radiation and said means for measuring the intensity of the beams after they pass through said item.

6. The apparatus of claim 1, further comprising means for generating a fourth incident beam of polychromatic X-ray radiation at a fourth tube excitation potential and for directing it toward said item.

7. The apparatus of claim 1, wherein said item is meat, one of said two components is fat, and said apparatus precludes any need to smooth a surface of said meat item.

8. The apparatus of claim 1, further including means for passing a plurality of said items to and away from said radiation generating means.

9. A method for determining the quantitative relationship of components in an item composed primarily of two components varying from each other in molecular makeup the method being capable of analyzing items variable in surface roughness, weight, density, thickness, and overall geometrical configuration comprising:

selecting a primarily 2-component item;

transmitting an incident beam of polychromatic X-ray radiation at a first preselected energy level through the item to develop an attenuated first beam;

transmitting a second incident beam of polychromatic X-ray radiation at a second preselected energy level through the item to develop an attenuated second beam;

transmitting a third incident beam of polychromatic X-ray radiation at a third preselected energy level through the item to develop an attenuated third beam;

measuring the intensity of each of the beams attenuated by said item;

calibrating said measured intensity of the incident beams and attenuated beams by using calibration constants of a set of calibration standards; and quantifying the relationship of the components in the item, said quantifying step including combining said three transmitting steps, said measuring step and said calibrating step to substantially eliminate effects of inaccuracies that are introduced by surface roughness of times and by polychromatic nature of said three beams.

10. The method of claim 9, wherein the lowest of said tube excitation potentials is not less than 20 KeVp.

11. The method of claim 9, wherein said item is meat and one of said two components is fat, and wherein said method includes precluding any need to smooth a surface of said meat item.

12. The method of claim 9, further comprising monitoring the incident beams to account for fluctuations in the incident beams.

13. The method of claim 9, wherein said calibrating step includes obtaining calibration standards attenuated beam readings by passing said first, second and third incident beams through said set of calibration standards, and calculating calibration constants for said item at each of said tube excitation potentials by correlating the respective intensity of each of said beams attenuated by said item with said calibration standards attenuated beam readings, respectively.

14. The method of claim 9, further comprising computing apparent component percentages by assuming that the item selected has smooth surfaces, and adjusting said apparent component percentages in conjunction with said calibrating step.

15. The method of claim 9, wherein said calibration standards are sandwiches of two materials having different molecular weights.

16. The method of claim 9, further comprising transmitting a fourth incident beam of polychromatic X-ray radiation at a fourth preselected tube excitation potential through the item to develop an attenuated fourth beam.

17. The method of claim 9, wherein the highest of said tube excitation potentials is not more than 120 KeVp.

18. The method of claim 9, wherein said selecting step includes choosing a plurality of said items that are analyzed in a generally continuous stream.

* * * * *